United States Patent
Duggan et al.

(10) Patent No.: US 6,641,824 B2
(45) Date of Patent: Nov. 4, 2003

(54) SKIN TREATMENT USING A NEW RETINOID

(75) Inventors: Michele Duggan, Middletown, NY (US); Lorraine M. Cowton, Cornwall, NY (US)

(73) Assignee: Avon Products, Inc., New York, NY (US)

( * ) Notice: Subject to any disclaimer, the term of this patent is extended or adjusted under 35 U.S.C. 154(b) by 76 days.

(21) Appl. No.: 10/039,745

(22) Filed: Nov. 9, 2001

(65) Prior Publication Data

US 2003/0092675 A1 May 15, 2003

(51) Int. Cl.[7] .............................. A61K 7/00; A61K 7/42; A61K 7/44; A61K 31/695; A61K 31/07
(52) U.S. Cl. ........................... 424/401; 424/59; 424/60; 424/400; 514/63; 514/725
(58) Field of Search ........................... 424/59, 60, 400, 424/401; 514/63, 725

(56) References Cited

U.S. PATENT DOCUMENTS

| | | |
|---|---|---|
| 3,000,939 A | 10/1961 | Pommer et al. |
| 3,060,229 A | 10/1962 | Eiter et al. |
| 3,932,665 A | 1/1976 | Van Scott et al. |
| 4,826,828 A | 5/1989 | Wilmott et al. |
| 4,934,114 A | 6/1990 | Lindsey |
| 2003/0044372 A1 * | 3/2003 | LeGrow .................. 424/70.12 |

* cited by examiner

*Primary Examiner*—Shelley A. Dodson
(74) *Attorney, Agent, or Firm*—Ohlant, Greeley, Ruggiero & Perle LLP

(57) ABSTRACT

There is provided a topical composition and method for improving the aesthetic appearance of skin, particularly, preventing, ameliorating, treating and/or reducing fine lines and/or wrinkles, without the skin irritation typically associated with topical application of a retinoid. The composition has an effective amount of retinoxytrimethylsilane. Preferably, the composition is applied daily to skin. The composition and method are particularly suitable for persons having sensitive skin.

22 Claims, No Drawings

SKIN TREATMENT USING A NEW RETINOID

BACKGROUND OF THE INVENTION

1. Field of the Invention

The present invention relates to the use of a novel retinoid, particularly a retinol derivative. More particularly, the present invention relates to the use of topical compositions having the retinol derivative, retinoxytrimethylsilane, to treat, including prevent, ameliorate and/or reduce, signs of dermatological aging, especially wrinkles, and/or improve the aesthetic appearance of skin. Still more particularly, the present invention provides the beneficial effects of retinol without causing skin irritation from daily use.

2. Description of the Prior Art

Retinoid or retinoid compounds/derivatives (collectively referred to herein as "retinoid" or "retinoids") are vitamin A derivatives. They are used in topical compositions to treat a variety of adverse skin conditions. Such skin conditions include acne, actinic damage, dandruff, eczema, fine lines, psoriasis, warts and wrinkles.

Retinoids used in the prior art include, but are not limited to, isotretinoin, retinal, retinol, retinoic acid, retinyl acetate, retinyl palmitate, retinyl propionate, synthetic retinoid mimics, and tretinoin. As is known in the art, the amount of retinoid in a topical composition varies depending on the condition to be treated, as well as on the composition and the retinoids themselves. Representative compositions having a retinoid are discussed, by way of example, in U.S. Pat. Nos. 3,006,939; 3,060,229; 3,932,665; 4,826,828; and 4,934,114.

However, topical compositions having a retinoid have been limited in the amount of retinoid, since retinoid has been found to irritate the skin. Such irritation is acute, especially when the amount of retinoid in the composition is high. However, some consumers with sensitive skin cannot even tolerate a small amount of retinoid.

The irritation can manifest itself in the form of physical discomfort and/or unaesthetic skin appearance. Such an unaesthetic skin appearance can manifest itself by dermatitis or erythema. The irritation may disturb the user to such an extent that the user will discontinue use of the composition having a retinoid. Alternately, the user may reduce the frequency of use, thereby possibly reducing the effectiveness of the composition for its intended purpose.

Heretofore, there has not been an efficacious skin care composition that contains a retinoid, but without the irritation induced by a retinoid. Historically, it has been observed that retinoid-induced skin irritation has a direct correlation to retinoid efficacy. Namely, the greater the concentration of retinol, the more likely that irritation will occur. Thus, simply reducing the retinoid concentration might decrease irritation to the skin, but it would also reduce the desired retinoid efficacy. Consumers require, and would benefit from, a retinol-delivering composition that is both well-tolerated and efficacious. The present composition having the retinoid, retinoxytrimethylsilane, achieves this need.

SUMMARY OF THE INVENTION

It is an object of the present invention to provide a topical composition having retinoxytrimethylsilane to treat, including prevent, ameliorate and/or reduce, signs of dermatological aging, especially wrinkles, and/or improve the aesthetic appearance of skin, and methods of its use.

It is another object to provide such a topical composition that is substantially anhydrous.

It is a further object of the present invention to provide a method for delivering the benefits of retinol without inducing irritation.

These and other objects and advantages of the present invention are achieved by a topical composition that has retinoxytrimethylsilane in an effective amount, preferably about 0.1 weight percent (wt %) to about 50 wt % of the total weight of the composition.

DETAILED DESCRIPTION OF THE INVENTION

The present invention relates to the surprising recognition that retinoxytrimethylsilane, a retinol derivative, delivers retinoid efficacy without skin irritation, dryness or erythema typically caused by the topical use of a retinoid. Further, it has also been discovered in the present invention that moisture-activated, retinol-delivering compositions having retinoxytrimethylsilane will treat, including prevent, ameliorate, and/or reduce, signs of dermatological aging, especially wrinkling and/or improve the aesthetic appearance of the skin upon daily application to skin. The composition is preferably applied topically once or twice daily. The daily application can be for periods up to two weeks, four weeks or more.

The present compositions preferably have an amount of retinoxytrimethylsilane from about 0.1 wt % to about 50 wt %, based on the total weight of the composition. More preferably, the present compositions have retinoxytrimethylsilane in an amount from about 0.5 wt % to about 15 wt %. Most preferably, the present compositions have retinoxytrimethylsilane in an amount from about 0.5 wt % to about 5 wt % of the total composition. To provide guidance to those skilled in the art for practicing the present invention, the efficacy of the retinol-derivative concentration in a topical composition is approximately equivalent to $10^{-1}$ concentration of retinol percent by weight of the composition. For example, to provide the efficacy of about 0.1 wt % (based upon the total weight of the composition) retinol activity, a composition of the present invention preferably includes about 1 wt % of retinoxytrimethylsilane.

In addition to improvements in skin care benefits of the present invention, the retinol-derivative, retinoxytrimethylsilane, results in more stable compositions than those of the prior art. This is evidenced by a lasting white color of the present compositions, without the manifestation of yellowing over time, particularly in a stick product form. The present compositions can also be in other cosmetic product forms, such as, for example, an emulsion, a gel, a lip balm, a lip gloss, a lotion, a mask, an ointment, a patch, a pomade, a solution, a spray, or a towelete.

The present compositions are preferably wax-based, oil-based, or silicone-based compositions, all of which are substantially anhydrous (i.e., contain less than about 1 wt %, more preferably no, water). Alternatively, the compositions may include greater than 1 wt % water as long as contact between the retinoxytrimethylsilane and water is prevented. For example, a two-phase product that is dispensed in a dual-chamber package with each phase in a separate chamber may include an aqueous phase in one chamber and the retinoxytrimethylsilane in substantially anhydrous phase in the other chamber. As the contents from each chamber are dispensed, the phases may combine either via the dispensing mechanism, as is known in the art, or mixed by the user as the user rubs the two phases onto and into the skin.

In a preferred embodiment of the present invention, the retinoxytrimethylsilane used is in soybean oil and is commercially available from Clariant Corp. under the tradename SilCare 1 M 75. The Clariant product is a 12% chemically reactive liquid derivative of retinol, which is readily dispersible in most substantially anhydrous organic cosmetic formulations at room temperature.

The compositions of the present invention yield improvements to the aesthetic appearance of the skin by treating, including preventing, ameliorating and/or reducing at least one of the following: dermatological aging, especially chronological, actinic or hormonal aging, skin fragility, loss of collagen and/or elastin, skin atrophy, skin dryness, skin flakiness, skin discoloration, skin sagging, signs of skin fatigue and/or stress, acne, psoriasis, eczema, and warts. In particular, improvements to the aesthetic appearance of skin include at least one of the following: makes facial lines appear less noticeable, makes facial lines and/or wrinkles feel plumped, improves appearance of suborbital lines and/or periorbital lines, improves appearance of crow's feet, reduces and/or diminishes the appearance of wrinkles, particularly facial wrinkles on the cheeks, forehead and/or around the mouth, and particularly deep wrinkles, rejuvenates and/or revitalizes skin, particularly aging skin, improves skin firmness and/or plumpness, improves skin tone, enhances skin thickness, decreases pore size, improves skin moisture and/or hydration, improves skin texture, reduces and/or eliminates fine and/or deep lines, smoothes skin, restores skin luster and/or brightness, and improves skin resiliency, flexibility and/or elasticity.

A preferred embodiment of the topical compositions of the present invention also includes at least one of the following: a surface smoother, a skin plumper, an optical diffuser, a sunscreen, an exfoliation promoter, and an antioxidant.

A surface smoother provides the functional benefits of enhancing skin smoothness and reducing the appearance of fine lines and coarse wrinkles. Examples include silicas, talcs, isopropyl myristate, petrolatum, isopropyl lanolate, silicones (e.g., methicone, dimethicone), polymethylmethacrylate (PMMA), or any mixtures thereof. The surface smoother is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

A sunscreen protects the skin from damaging ultraviolet rays. In an illustrative embodiment of the present invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. Preferably, the sunscreen is present from about 1 wt % to about 30 wt % of the total weight of the composition. In particular, the addition of a sunscreen is preferred to prevent/reduce the photodegradation of retinoid while in the package and/or on the skin.

The compositions of the present invention having sunscreen bring about additional improvements to the aesthetic appearance of skin, including at least one of the following: minimizes sunburning, minimizes tanning, and reduces redness.

The present compositions may also have one or more exfoliation promoters. Suitable examples of an exfoliation promoter that can be used in the present compositions include alpha hydroxy acids; benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; stearoxytrimethylsilane (available from Clariant under the tradename SILCARE 1 M 71); trimethylsilyl trimethylsiloxy glycolate (available from Clariant under the trade name SILCARE 180 M 30); trimethylsilyl trimethylsiloxy lactate (available from Clariant under the tradename SILCARE 180 M 10); urea; or any mixtures thereof. The preferred exfoliation promoters are 3,6,9-trioxaundecanedioic acid, glycolic acid, lactic acid, or any mixtures thereof.

When the present invention includes an exfoliation promoter, the composition has about 1 wt % to 20 wt %, preferably about 1 wt % to about 15 wt %, more preferably about 4 wt % to about 10 wt %, and most preferably about 4 wt %, of the exfoliation promoter based on the total weight of the composition.

An antioxidant functions, among other things, to scavenge free radicals from skin to protect the skin from environmental agressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt %, and more preferably from about 0.001 wt % to about 5 wt %, of the total weight of the composition.

The present composition may also have one or more of the following ingredients or adjuvants: anesthetics, antiallergenics, antifungals, antiseptics, chelating agents, colorants, demulcents, emollients, emulsifiers, fragrances, humectants, lubricants, moisturizers, pH adjusters, pigment altering agents, preservatives, skin penetration enhancers, stabilizers, surfactants, thickeners, viscosity modifiers, vitamins, or any mixtures thereof.

The component(s) of the present invention are preferably contained in a cosmetically acceptable vehicle. Suitable vehicles of the present invention may also include mineral oil, petrolatum, polydecene, and vegetable oil.

To form the exemplary wax-based stick products of the present invention, processing is undertaken at typical temperatures for that type of base (e.g., about 150° F. to about 170° F.), over extended periods of time. Higher temperatures are feasible due to greater stability of the retinol-derivative of the current invention as compared to active retinol. Also, processing at room temperature is a suitable means for forming the compositions of the present invention. In short, the present compositions can be processed from room temperature just up to about 180° F., even though about 150° F. to about 170° F. is preferred.

The following is an illustrative, non-limiting example of a composition of the present invention.

EXAMPLE

A facial treatment stick composition of the present invention was prepared comprising the following ingredients: about 0.1 wt % retinoxytrimethylsilane, soja (soybean) oil, methicone, PPG-5-ceteth-20, octyl methoxycinnamate, palmitoyl oligopeptide, zinc oxide, titanium dioxide, petrolatum, methylparaben, aluminum hydroxide, polydecene, benzoic acid, isopropyl myristate, isopropyl lanolate, ozokerite, tocopheryl acetate, and silica.

This inventive composition was compared to two products: (1) a wrinkle cream available from Johnson & Johnson under the combined tradename Roc™ Actif Pur™ and (2) a generic retinol cream. The Roc™ product has the following ingredients: about 0.1 wt % retinol, water, octyl hydroxystearate, ceteareth-20, glycerin, glyceryl distearate, dimethicone, C12-15 alkyl lactate, steareth-10, stearyl alcohol, sodium citrate, cholesterol, cetearyl alcohol, acetylated lanolin, phenoxyethanol, polysorbate 80, methylparaben, polyacrylamide, disodium EDTA, propylparaben, cetyl acetate, laureth-7, polysorbate 20, BHT, C13-14 isoparaffin, ascorbic acid, and BHA. The generic retinol cream has the following ingredients: about 0.1 wt % retinol, water, carbopol 934, disodium EDTA, veegum, glycerin, propylene glycol, emulsifying wax, cetyl ricinoleate, cetyl alcohol, C10-30 cholesterol/lanosterol esters, stearic acid, POE (10M) soya sterol, methylparaben, triethanolamine, dimethyl polysiloxane, and benzyl alcohol.

There was a two-week, double-blind, split-face, baseline controlled study conducted at an independent laboratory on a population with clinically sensitive skin, in which each composition was applied once daily. This study compared the composition of the present invention to the two products identified above.

Forty women participated in this study. The forty women ranged in age from 29 to 64 years. The panelists were required to have clinically sensitive skin (i.e., atopic and/or rosacea) background. Dermatological examinations for irritation attributes were conducted at baseline, one and two weeks. Each panelist applied all three products on their face once daily in the morning. The test products were identified to enhance compliance.

Table 1 indicates that the composition of the present invention significantly improved dryness and erythema (redness) at two weeks, while Roc™ and the generic retinol cream significantly worsened both conditions (indicated by a negative number). In addition, the composition of the present invention improved the condition of papules/pustules as compared to the generic retinol cream, and significantly improved the same condition as compared to the Roc™ product, which instead significantly worsened the condition.

TABLE 1

Comparison of Magnitude of Change from baseline in Dermatologist Score

| Improvement Parameter | Present Invention % Δ @ Week 2 | Roc % Δ @ Week 2 | Generic Cream % Δ @ Week 2 |
| --- | --- | --- | --- |
| Dryness | 26% | −38% | −15% |
| Erythema | 15% | −19% | −17% |
| Papules/Pustules | 50% | −33% | 33% |

As Table 2 shows, the dermatologist observed that at two weeks, dryness either decreased or remained the same in all panelists using the composition of the present invention, while 73% of the subjects using Roc™ showed an increase in dryness. Thirty-three percent of the panelists using the generic retinol cream also had an increase in dryness. Ninety-three percent of the panelists using the composition of the present invention showed either a decrease or no change in erythema (redness), while 42% of panelists using Roc™ and 37% of panelists using the generic retinol cream showed increased erythema.

TABLE 2

% of Panelist Improving or Declining

| Improvement Parameter | Present Invention % Δ @ Week 2 | Roc % Δ @ Week 2 | Generic Cream % Δ @ Week 2 |
| --- | --- | --- | --- |
| Decrease in Dryness | 54% | 8% | 15% |
| Increase in Dryness | 0 | 73% | 33% |
| Dryness Remained the Same | 46% | 19% | 52% |
| Decrease in Erythema | 41% | 8% | 0% |
| Increase in Erythema | 7% | 42% | 37% |
| Erythma Remained the Same | 52% | 50% | 63% |

As is evident, the composition of the present invention significantly improved erythema and dryness after two weeks of use, whereas Roc™ and the generic retinol cream significantly exacerbated both conditions. This is indicated by both magnitude of change and percent of panel improving or declining. These are impressive findings because increases in skin surface texture changes (dryness) and erythema (redness) are typical in the first 2 to 3 weeks of topical retinoid use. In addition, all of the panelists were clinically sensitive-skinned individuals.

Thus, the composition of the present invention decreased dryness and erythema (redness), while the Roc™ and generic retinol cream significantly increased the same attributes. Therefore, the composition of the present invention is superior to the prior art for treating sensitive skin.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

What is claimed is:

1. A method of treating fine lines and/or wrinkles, comprising applying to skin a topical, substantially anhydrous composition having an amount of retinoxytrimethylsilane effective to prevent, ameliorate and/or reduce fine lines and/or wrinkling.

2. The method of claim 1, wherein said composition is applied for a period of time effective to prevent, ameliorate and/or reduce fine lines and/or wrinkling.

3. The method of claim 2, wherein said applying of the composition occurs once or twice daily up to two or four weeks.

4. The method of claim 1, wherein said retinoxytrimethylsilane is present in an amount from about 0.1 wt % to about 50 wt % of the total weight of the composition.

5. The method of claim 1, wherein said retinoxytrimethylsilane is present in an amount from about 0.5 wt % to about 15 wt % of the total weight of the composition.

6. The method of claim 1, wherein said retinoxytrimethylsilane is present in an amount from about 0.5 wt % to about 5 wt % of the total weight of the composition.

7. The method of claim 1, wherein said composition further comprises a cosmetically acceptable vehicle.

8. A method of improving the aesthetic appearance of skin comprising topically applying to skin a substantially anhydrous composition having retinoxytrimethylsilane in an amount effective to improve the aesthetic appearance of skin.

9. The method of claim 8, wherein the improvement in aesthetic appearance is selected from the group consisting of makes facial lines appear less noticeable, makes facial lines and/or wrinkles feel plumped, improves appearance of suborbital lines and/or periorbital lines, improves appearance of crow's feet, reduces and/or diminishes the appearance of wrinkles, rejuvenates and/or revitalizes skin, improves skin firmness and/or plumpness, improves skin tone, enhances skin thickness, decreases pore size, improves skin moisture and/or hydration, improves skin texture, reduces and/or eliminates fine and/or deep lines, smoothes skin, restores skin luster and/or brightness, and improves skin resiliency, flexibility and/or elasticity.

10. The method of claim 8, wherein the improvement in aesthetic appearance is the treatment of at least one condition selected from the group consisting of dermatological aging, skin fragility, loss of collagen and/or elastin, skin atrophy, skin dryness, skin flakiness, skin sagging, skin discoloration, signs of skin fatigue and/or stress, acne, psoriasis, eczema, and warts.

11. The method of claim 10, wherein said dermatological aging is selected from the group consisting of chronological aging, actinic aging, hormonal aging, or any combinations thereof.

12. The method of claim 8, wherein said skin is sensitive skin.

13. The method of claim 8, wherein said appearance of skin is substantially free of skin irritation.

14. A method of improving the aesthetic appearance of skin comprising topically applying to skin a substantially anhydrous composition having retinoxytrimethylsilane, in an amount and for a period of time sufficient to improve the aesthetic appearance of skin.

15. The method of claim 14, wherein said applying of the composition occurs once daily or twice daily up to two or four weeks.

16. A topical, substantially anhydrous composition comprising retinoxytrimethylsilane in an amount effective to prevent, ameliorate, reduce and/or treat fine lines and/or wrinkles.

17. The composition of claim 16, wherein said retinoxytrimethylsilane is present in an amount from about 0.1 wt % to about 50 wt % of the total weight of the topical composition.

18. The composition of claim 16, wherein said retinoxytrimethylsilane is present in an amount from about 0.5 wt % to about 15 wt % of the total weight of the composition.

19. The composition of claim 16, wherein said retinoxytrimethylsilane is present in an amount from about 0.5 wt % to about 5 wt % of the total weight of the composition.

20. The composition of claim 16, further comprising a cosmetically acceptable vehicle.

21. The composition of claim 16, further comprising an antioxidant.

22. The composition of claim 16, further comprising a sunscreen.

* * * * *